United States Patent [19]

Fiege et al.

[11] 4,144,400
[45] Mar. 13, 1979

[54] PROCESS FOR THE CONTINUOUS PREPARATION OF DI-TERTIARY BUTYLCRESOLS

[75] Inventors: Helmut Fiege; Josef Haydn; Johann Renner, all of Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 748,073

[22] Filed: Dec. 6, 1976

[30] Foreign Application Priority Data

Dec. 24, 1975 [DE] Fed. Rep. of Germany ....... 2558522

[51] Int. Cl.$^2$ ............................................. C07C 39/06
[52] U.S. Cl. .................................................. 568/788
[58] Field of Search ...................... 260/624 R, 624 C; 568/788

[56] References Cited

U.S. PATENT DOCUMENTS 3,534,111  10/1970  Hess ................................. 260/624 R

OTHER PUBLICATIONS

Weinrich "Ind & Eng. Chem" vol. 35, pp. 264–272 (1943).

Primary Examiner—James O. Thomas, Jr.
Assistant Examiner—Werren B. Lone
Attorney, Agent, or Firm—Sprung, Felfe, Horn, Lynch & Kramer

[57] ABSTRACT

A process for the continuous preparation of a ditertiary butylcresol wherein m- or p-cresol is reacted with isobutene at elevated temperature using $H_2SO_4$ as catalyst wherein the process is carried out stepwise by introducing stepwise into a reaction mixture comprising substantially all of the cresol to be reacted with isobutene. The total amount of isobutene introduced is introduced such that less isobutene is charged in a last stage of the process than in the first stage thereof. Thereafter the catalyst is deactivated.

9 Claims, No Drawings

PROCESS FOR THE CONTINUOUS PREPARATION OF DI-TERTIARY BUTYLCRESOLS

The invention relates to a process for the continuous preparation of di-tert.-butylcresols from m-cresol and/or p-cresol and isobutene.

Because the boiling points of m-cresol and p-cresol lie close together it is not possible to separate mixtures of m-cresol and p-cresol by distillation. However, the di-tert.-butyl-substituted compounds can readily be separated by distillation and converted into the pure cresols by subsequent dealkylation (Ind. Engng. Chem. 35, pages 655 to 660). Furthermore, 2,6-di-tert.-butyl-p-cresol is a widely used anti-ageing agent (Ullmann, 3rd edition, Supplementary Volume, page 196) and 4,6-di-tert.-butyl-m-cresol also can be used as such an agent (JA-AS (Japanese Published Specification) No. 73/43,185).

Therefore, continuous processes which operate with a high yield and with which the amount of by-products obtained is small are of particular importance for the economical large scale industrial production of di-tert.-butylcresols.

The continuous preparation of di-tert.-butylcresols by reacting m-cresol and/or p-cresol with isobutene at elevated temperature, using sulphuric acid as the catalyst, in packed columns or bubble cap tray columns is known from Ind. Engng. Chem. 35, pages 264–272 (1943). The columns are operated in counter-current, that is to say cresol, to which sulphuric acid has been added, is metered in from the top and isobutene in the gas form — for example in the form of a $C_4$ cut containing about 20% of isobutene — flows from below in counter-current to the cresol. The isobutene concentration is thus the greater the further the alkylation has already progressed. In order to increase the partial pressure of the isobutene, and thus to increase the rate of reaction, the reaction is carried out under pressure (5 to 6 atmospheres gauge).

The amount of sulphuric acid added is 5% by weight, based on cresol, and the amount of $H_2SO_4$ may be changed only within a very narrow range; amounts of less than 3% by weight reduce the degree of alkylation and amounts of more than 5% by weight lead to extensive side reactions. Moreover, the sulphuric acid leads to losses of cresol due to sulphonation to cresolsulphonic acids and these losses are proportional to the amount of sulphuric acid.

85° C. is quoted as the optimum temperature for the lower part of the counter-current column and 96° C. is quoted as the optimum temperature for the upper part. In order to be able to maintain this vertical temperature gradient and to avoid horizontal temperature gradients, the bubble cap trays must be cooled in a very expensive manner so that the considerable heat of reaction of the alkylation — about 175 kcals/kg of crude alkylate — can be removed; here and in the text which follows alkylate is to be understood as the reaction product obtained from the alkylation. The space-time yield is relatively low, being only about 0.1 kg of crude alkylate per liter, per reaction space and per hour.

The composition of the crude alkylate which is withdrawn from a counter-current column with 15 bubble cap trays under the abovementioned conditions is given in Table 1.

Table 1

| | |
|---|---|
| 6.2% of polybutenes (mainly triisobutene) | |
| 23.8% of monobutylcresols | |
| 28.1% of dibutyl-p-cresol | ⎫ |
| 37.9% of dibutyl-m-cresol | ⎬ 66.0% |
| 4.0% of residues | ⎭ |

Accordingly, the dibutyl-cresol content of the mixture is only 66% by weight. A relatively large amount of polybutene, and especially triisobutene, is formed and this makes it more difficult to separate off the monobutylcresols — which can be recycled into the alkylation.

The 5% by weight of $H_2SO_4$ employed in this process lead to a loss of about 5% by weight of the amount of cresols employed. Sulphur-containing, tarry by-products are formed and these make up about half of the crude alkylate residue in Table 1 and are a drawback to the process.

Thus, both with regard to the yield of dibutylcresols, the amount of monobutylcresols to be recycled, the proportion of by-products which cannot be utilised and the losses of cresol and with regard to the type of reactor and its space-time yield, the continuous process according to the state of the art has numerous disadvantages which severely restrict its usefulness.

SUMMARY OF THE INVENTION

Broadly, this invention contemplates an improvement in the process for the continuous preparation of a di-tert.-butylcresol wherein m-cresol or p-cresol is reacted with isobutene at elevated temperature in the presence of $H_2SO_4$ as catalyst the improvement residing in carrying out the process stepwise by introducing stepwise into a reaction mixture comprising substantially all of the cresol to be reacted isobutene, the total amount of isobutene introduced being introduced stepwise such that less isobutene is introduced in a last step of the process than introduced in the first step thereof and thereafter deactivating the catalyst.

It has now been found that di-tert.-butylcresols can advantageously be prepared continuously by reacting m-cresol and/or a mono-tert. butylcresol with isobutene at elevated temperature, using sulphuric acid as the catalyst, the reaction being carried out stepwise in such a way that all of the cresol is fed in at a first step of the reaction, and the total amount of isobutene employed being so distributed that less isobutene is fed in at the last step of the reaction than is fed in at the first step, the catalyst subsequently being deactivated.

In general, the process is carried out at temperatures below 80° C. and preferably in the temperature range from 50°–70° C.

The apparatuses used for carrying out the process stepwise, according to the invention, are those which, in accordance with their residence time characteristics, approach an ideally mixed stirred kettle for each stage; apparatuses of this type are termed mixing reactors for each stage in the text which follows.

Accordingly, all of the apparatuses known according to the state of the art which meet the above condition can be used for carrying out the process according to the invention. Apparatuses of this type are known, for example, from Ullman, Encyklopädie der Technischen Chemie (Encyclopedia of Industrial Chemistry), 4th edition (1973), volume 3, page 321 et seq., especially pages 342 to 354 and 357 to 394, and are familiar to all those skilled in the art. For example, suitable mixing reactors which may be mentioned are stirred kettles and loop reactors which have a high circulation; according to the above definition, even a tower reactor may be regarded as a series of mixing reactors.

A mixing reactor cascade, that is to say a number of mixing reactors connected in series, may be used for carrying out the process stepwise, according to the invention. In general, the mixing reactor cascade consists of 2 to 7, and preferably 3 to 4, mixing reactors connected in series. The reaction in each mixing reactor constitutes one step of the overall reaction.

The cascade can consist of individual mixing reactors which may be of the same or different design and are connected in series. The mixing reactors can also be located in a common housing. The individual reactors of the cascade can be of the same size or of different sizes. Reactors of the same size are preferred. The reactor cascade can be operated as an open cascade or a flooded cascade. Austenitic steels are suitable as the construction material.

The heat of reaction can be removed via the cooling jacket of the reactor, by means of internal cooling and/or by circulation through external coolers. In the latter case, the circulating pump can optionally wholly or partly replace a stirrer. Cooling can also be assisted by feeding all or part of the isobutene as a liquid into the mixing reactors, so that its heat of vaporisation contributes to the removal of the heat of reaction.

The starting compounds in the process of the invention that is to say m- and p-cresol and isobutene, are known. In addition to m- and p-cresol and the mixtures of cresols thus obtained, it is also possible to use mono-tert.-butylcresols of m-cresol and p-cresol, on their own and as a mixture with m-cresol and/or p-cresol, as the starting compounds. The cresols are metered into the first reactor of the cascade; the mono-tert.-butylcresols can also be metered into another reactor of the cascade but the 1st reactor of the cascade is preferred.

Isobutene can be employed in the pure form or as a mixture with other substances which do not react with cresol or which react with the latter more slowly than isobutene, for example so-called $C_4$ hydrocarbon cuts. The use of substantially pure isobutene is preferred.

Isobutene can be employed both as a liquid and in the gas form; it can be advantageous to use a liquid isobutene or isobutene mixture in order to remove part of the heat of reaction, which is generated during the reaction, by means of the heat of vaporisation of the liquid isobutene.

In general, concentrated 96–98% strength by weight sulphuric acid (remainder water) is used as the sulphuric acid. However, the concentration can also be higher, especially when small amounts of water in the feed material are to be compensated, that is to say it is also possible to use oleum or $SO_3$.

The amount of sulphuric acid to be used depends both on the water content of the cresol employed and on the concentration of the sulphuric acid. For example, when the water content in the cresol employed is less than 0.1% by weight, an appropriate amount of sulphuric acid is 2.0% by weight, based on the cresol employed, of 96 to 98% strength by weight sulphuric acid. However, if cresol which has a higher water content is used, the amount of $H_2SO_4$ must then be correspondingly increased; this can be effected either by using more sulphuric acid or by using sulphuric acid of a higher concentration, for example oleum or sulphur trioxide, which reacts with the water present to form $H_2SO_4$. In general, less than 3% by weight of $H_2SO_4$, and preferably 0.5 to 2% by weight of $H_2SO_4$, based on anhydrous cresol, are used.

The sulphuric acid either can be metered continuously on its own into the first cascade stage or can already previously be mixed with cresol or with the cresol/mono-tert.-butylcresol mixture, or with proportions of these feed materials.

According to the invention, the catalyst is deactivated after the end of the reaction, that is to say in the reaction product which issues from the final stage of the cascade. This deactivation must be effected as soon as possible, preferably within 30 minutes. As has been mentioned, sulphuric acid, oleum or $SO_3$ is customarily used as the catalyst; however, as is known these compounds react very readily with phenols to give the corresponding sulphonic acids which, in turn, also have a catalytic action, so that generally catalytically active acid substances in the alkylate must be deactivated.

The deactivation of the catalyst can be carried out in a manner which is in itself known, for example it can already be effected by cooling the reaction mixture, for example to below 35° C., or by the addition of water and/or basic substances. Basic substances which can be used are all substances which are sufficiently basic to deactivate the acid catalyst, for example by forming a salt.

Examples of substances which can be used are oxides, hydroxides, carbonates and bicarbonates, especially of the alkali metals and alkaline earth metals, but also ammonia and amines.

The catalyst is preferably deactivated by adding water or aqueous solutions of alkali metal hydroxides and alkali metal carbonates and also of alkaline earth metal hydroxides; the decisive reasons for this are in particular those of expediency, since water and aqueous solutions can generally be separated off more easily and, furthermore, the removal of, for example, amines from the reaction product would again involve more effort.

Of course, the deactivation of the catalyst in the manner according to the invention can also be effected by washing out, which is in itself known, with, for example, dilute aqueous sodium hydroxide solution.

However, it is essential that the catalyst is deactivated as soon as possible after the end of the reaction, especially when m-cresol has been converted. Such as within 60 minutes, preferably within 30 minutes. The reason for this is that, according to our own experience, a reaction product which contains di-tert.-butyl-m-cresol is not stable in the presence of the catalyst but is split again to give mono-tert.-butyl-m-cresol and isobutene, which, in turn, polymerises to polybutene. This redissociation takes place to a considerably lesser extent in the case of the corresponding p-compound.

In general, the process of the invention may be carried out as follows.

All of the cresol, the chosen amount of sulphuric acid and part of the isobutene are metered in to the first mixing reactor of the cascade.

The cascade preferably consists of 3 or 4 mixing reactors.

Of course, it is also possible to provide the cascade with only 2, or with more than 4, for example 5, 6 or 7, reactors. It is economical rather than technical considerations which are decisive for the appropriate choice of the number of reactors. In the case of a smaller number of reactors, a reduction in the yield of di-tert.-butylcresol and increased formation of aliphatic compounds and mono-tert.-butylcresols must be accepted and in the case of a relatively large number of reactors the disadvantage of higher investment and operating costs can outweigh the advantage of a better yield.

In general, the reaction temperature in the mixing reactors is below 80° C. and preferably between 50° and 70° C.; within these limits it can also be different, and vary, in the individual mixing reactors. An almost isothermal procedure at 60° C. can be particularly advantageous.

The total residence time of the reaction mixture in the mixing reactor cascade should, in general, be not more than 5 hours. Total residence times of between one and four hours can be advantageous.

The reaction can be carried out under normal pressure, elevated pressure or reduced pressure. Isobutene partial pressures in the reactors of 0.1 to 2 bars can be advantageous. The isobutene partial pressure in the individual reactors can be the same or different. A procedure with which the isobutene partial pressure is approximately the same in all the reactors can be particularly advantageous.

The molar ratio of the total amount of isobutene employed to cresol can be about 1.7 : 1 up to 2.0 : 1. In general, a ratio of about 1.8 : 1 up to 1.95 : 1 is preferred and, in particular, a ratio of about 1.9 : 1 will be advantageous.

The percentage distribution of the total amount of isobutene to be metered in between the individual mixing reactors of the cascade must be made in such a way that the amount of isobutene metered into the final reactor is less than the amount of isobutene metered into the first reactor. A distribution in which the amount of isobutene metered in becomes smaller from reactor to reactor is preferred. A distribution in which the amount of isobutene metered in to a particular mixing reactor is at most half that metered into the preceding reactor is particularly preferred. If mono-tert.-butylcresol is fed to one of the mixing reactors, the amount of isobutene to be fed into that particular reactor must be reduced by the amount of isobutene bound in the mono-tert.-butylcresol.

The process can be conducted, for example, by introducing the isobutene to the several stages stepwise.

If only two steps are employed between 55 and 85%, preferably between 70 and 85% of the total isobutene is introduced in the first step and between 15 and 45%, preferably between 15 and 30% is introduced in the second step.

If three steps are employed between 35 and 80%, preferably between 55 and 75% of the total isobutene is introduced in the first step, between 10 and 40%, preferably between 15 and 30% is introduced in the second step and between 4 and 32%, preferably 5 and 20% is introduced in the third step.

If four steps are employed between 30 and 75%, preferably between 50 and 70% of the total isobutene is introduced in the first step, between 10 and 40%, preferably between 15 and 30% is introduced in the second step, between 5 and 31%, preferably 5 and 20% is introduced in the third step and between 2 and 20%, preferably between 2 and 10% is introduced in the fourth step.

If five steps are employed between 25 and 70%, preferably between 40 and 60% of the total isobutene is introduced in the first step, between 10 and 40%, preferably between 15 and 30% is introduced in the second step, between 5 and 30%, preferably between 5 and 20% is introduced in the third step, between 2 and 20%, preferably between 2 and 15% is introduced in the fourth step and between 1 and 15%, preferably between 1 and 10% is introduced in the fifth step.

In all cases the amount of isobutene introduced in the first stage is greater than that introduced in the last stage. The amount of isobutene in any intermediate stages can reduce stepwise from the first step to the last.

For example, the process according to the invention can advantageously be carried out as described below.

A cascade which consists of four intensively mixed stirred kettles which are connected in series and joined by overflows and which all have approximately the same reaction volume and are connected to the outside atmosphere by means of an off-gas line and are kept at the same temperature by means of water cooling is used.

2% by weight of concentrated sulphuric acid (96 to 98% by weight of $H_2SO_4$, remainder water), for example, are added to cresol or a mixture of m-cresol and p-cresol, for example in a ratio of 70:30, and the resulting mixture is pumped continuously into the first kettle.

Isobutene is used, for example, in a ratio of 1.9 mols of isobutene: 1 mol of cresol and, in the case of a cascade with 4 reactors, is, for example, so distributed that, per unit time, 60% of the total amount are metered into the first reactor, 24% of the total amount are metered into the second reactor, 11% of the total amount are metered into the third reactor and 5% of the total amount are metered into the last reactor.

According to the invention, the catalyst is deactivated after the end of the reaction. As already mentioned, this can be effected by cooling the reaction mixture, for example to below 35° C., by admixing water or an aqueous alkali solution or also by employing both measures. It is essential that the catalyst is deactivated as soon as possible after the reaction mixture has left the reactor cascade.

The technical advance achieved by the process according to the invention is shown as follows.

Although the reaction is carried out at a lower temperature and using less sulphuric acid and is not carried out in counter-current, the continuous process according to the invention, compared with the process according to the state of the art, surprisingly gives di-tert.-butylcresols — in particular di-tert.-butyl-m-cresol — in a higher yield and with the formation of a smaller amount of by-products (polybutenes) which cannot be utilised. The proportion of monobutylcresols is lower and, due to the fact that the proportion of triisobutene is also lower, these monobutylcresols can be separated off more easily. Furthermore, the losses of cresol are lower, temperature control is more simple and the space-time yield is several times greater.

EXAMPLES 1-14

In the examples which follow a reactor cascade which consisted of 4 intensively mixed stirred kettles which were connected in series and joined by overflows and which all had approximately the same reaction volume and were connected to the outside atmosphere by means of an off-gas line was used; the stirred kettles were kept at approximately the same internal temperature, which is indicated in Table 2 which follows, by means of water cooling.

The mixture of cresols employed consisted of 30% of p-cresol and 70% of m-cresol. Per hour, 510 parts by weight of the mixture of cresols, to which 2% by weight of concentrated sulphuric acid had been added, were metered into the first kettle.

The isobutene used was an industrially pure gas of about 99% purity. The amount employed per hour was 1.9 mols per mol of cresol.

The total amount of isobutene metered in per unit time was distributed in accordance with the percentage ratio indicated in Table 2 and metered continuously into the liquid reaction mixture in the particular stirred kettle.

The average residence time in the final kettle of the cascade was 0.46 hour and the space-time yield, based on the total cascade, was about 500 g of alkylate per liter of reaction space and per hour.

In the steady state of operation, samples were taken of the reaction mixture flowing out of the final stage of the cascade and immediately washed with sodium carbonate solution and then analysed by gas chromatography.

Table 2 which follows gives the reaction temperature, which, of course, represents only the average value of the customary and unavoidable variations in the actual temperature within each individual kettle and between the different kettles, the percentage distribution of the total amount of isobutene between the different kettles and the composition, in % by weight according to the analysis by gas chromatography, of the reaction mixture which flows out in the steady state and also, separately, the sum of the aliphatic compounds and di-tert.-butylcresols in % by weight of the total mixture, for each of Examples 1–14.

EXAMPLE 15

In this example a cascade which consisted of only three kettles of equal size but was otherwise of the same type as that used in Examples 1–14 was used. The residence time in the final kettle of the cascade was 0.46 hour and the space-time yield, based on the total cascade, was 670 g of alkylate per liter of reaction space and per hour. In other respects the reaction was carried out as in Examples 1–14: the reaction parameters and the result are also given in Table 2.

EXAMPLES 16 and 17 (Comparison Examples)

In these examples all of the isobutene was fed into only one continuously operating stirred kettle, into which the mixture of cresols which was used in the above examples and to which 2% by weight of concentrated sulphuric acid had been added, had been metered.

In order to make it possible to react cresol and isobutene, in a ratio of 1:1.9, in this single kettle, the residence time was lengthened to 2.9 hours; as a result, the space-time yield was only about 300 g of alkylate per liter of reaction space and per hour.

Sampling and the working up of the reaction mixture were carried out as described above and the reaction temperature and the composition of the reaction product are likewise given in Table 2 which follows.

EXAMPLE 18 (Comparison Example)

In this example a counter-current column 180 cm in height and 2.8 cm in diameter, which was filled with 2 × 4 mm glass rings and in which the temperature was kept constant by means of a jacket cooler through which water flowed as the heat carrier, was used.

The mixture of cresols described above, with 2% by weight of concentrated $H_2SO_4$, was fed in from the top and 99% pure isobutene (1% of foreign gas) was fed in from below in counter-current. The molar ratio of isobutene:cresol was kept at 1.9:1.0 and the throughput was so adjusted that, in steady operation, the amount of off-gas corresponded exactly to the proportion of foreign gas in the isobutene, that is to say the column was utilised in an optimum manner. This gave a space-time yield of about 100 g of alkylate per liter of reaction space and per hour; the volume of the glass rings has not been taken into account.

The reaction product was withdrawn from the bottom of the column and worked up in the manner described above.

The reaction temperature and the composition of the reaction product are also given in Table 2 which follows.

EXAMPLE 19

The reaction was carried out as described in Example 12 and a sample of the reaction mixture was withdrawn, in the steady state, at the outlet of the reactor cascade.

A portion of this sample was washed direct with 5% strength by weight aqueous sodium carbonate solution and then examined by gas chromatography. Further portions of the sample were washed with the sodium carbonate solution only after they had been stored at 70° C. for 0.5, one, two and four hours and were then immediately analysed by gas chromatography.

The analytical results obtained are summarized in Table 3 which follows.

Table 2

| Example No. | Temperature ° C | Distribution, in %, of isobutene between the kettles Kettle No. | | | | Composition of the reaction mixture in the steady state at the outlet (in % by weight) | | | | | | |
|---|---|---|---|---|---|---|---|---|---|---|---|---|
| | | 1 | 2 | 3 | 4 | t.-butanol | iso-butene | diiso-butene | triiso-butene | cresol | cresol ether | mono-t.-butyl-cresols |
| 1 | 60 | 25 | 25 | 25 | 25 | 2.1 | 0.8 | 2.1 | 0.5 | 0.2 | 1.4 | 17.0 |
| 2 | 60 | 27 | 27 | 27 | 19 | 1.5 | 0.7 | 2.1 | 0.5 | 0.1 | 1.4 | 16.3 |
| 3 | 60 | 40 | 30 | 20 | 10 | 1.6 | 0.3 | 1.7 | 0.5 | 1.1 | 1.1 | 15.3 |
| 4 | 60 | 40 | 40 | 15 | 5 | 1.6 | 0.3 | 1.8 | 0.8 | 0.5 | 0.5 | 15.2 |
| 5 | 60 | 50 | 30 | 15 | 5 | 1.3 | 0.4 | 1.7 | 0.6 | 0.4 | 0.6 | 14.5 |
| 6 | 60 | 60 | 20 | 15 | 5 | 1.3 | 0.4 | 1.6 | 0.7 | 0.5 | 0.4 | 14.0 |
| 7 | 60 | 60 | 24 | 11 | 5 | 1.2 | 0.3 | 1.6 | 0.6 | 0.2 | 0.3 | 13.0 |
| 8+ | 60 | 60 | 24 | 11 | 5 | 1.2 | 0.4 | 1.6 | 0.7 | 0.1 | 0.4 | 13.4 |
| 9 | 40 | 60 | 24 | 11 | 5 | 1.3 | 0.9 | 2.6 | 0.7 | 0.6 | 3.8 | 12.1 |
| 10 | 50 | 60 | 24 | 11 | 5 | 1.4 | 0.4 | 1.7 | 0.6 | 0.3 | 1.2 | 12.1 |
| 11 | 60 | 60 | 24 | 11 | 5 | 1.2 | 0.3 | 1.6 | 0.6 | 0.2 | 0.3 | 13.0 |
| 12 | 70 | 60 | 24 | 11 | 5 | 1.2 | 0.2 | 1.7 | 0.9 | 0.1 | — | 15.7 |
| 13 | 80 | 60 | 24 | 11 | 5 | 0.8 | 0.1 | 2.0 | 1.7 | <0.1 | — | 21.2 |
| 14 | 90 | 60 | 24 | 11 | 5 | 0.7 | 0.1 | 2.5 | 2.4 | <0.1 | — | 26.4 |

Table 2-continued

| | | | | | | | | | | | | |
|---|---|---|---|---|---|---|---|---|---|---|---|---|
| 15 | 60 | 68 | 24 | 8 | — | 1.4 | 0.4 | 2.0 | 1.1 | 0.1 | 0.7 | 13.9 |
| 16++ | 60 | 100 (only one stirred) kettle) | | | | 1.6 | 0.4 | 3.7 | 3.2 | 0.4 | 1.8 | 13.2 |
| 17++ | 80 | 100 | | | | 1.2 | 0.3 | 3.2 | 3.9 | 0.9 | 0.5 | 20.7 |
| 18++ | 60 | counter-current column | | | | 1.7 | 0.3 | 2.2 | 0.9 | 0.3 | 3.5 | 17.5 |

+isobutene metered in as a liquid
++comparison examples

| | Composition of the reaction mixture in the steady state at the outlet (in % by weight) | | | | Sum (% by weight of the reaction mixture) | |
|---|---|---|---|---|---|---|
| Example No. | intermediate product | di-tert.-butyl-p-cresol | di-tert.-butyl-m-cresol | high-boiling compounds | aliphatic compounds | di-tert.-butyl-cresols |
| 1 | 0.1 | 25.6 | 49.7 | 0.5 | 5.5 | 75.3 |
| 2 | 0.2 | 25.8 | 50.9 | 0.5 | 4.8 | 76.7 |
| 3 | 0.1 | 26.9 | 51.5 | 0.5 | 4.1 | 78.4 |
| 4 | 0.1 | 27.2 | 51.6 | 0.4 | 4.1 | 78.9 |
| 5 | <0.1 | 27.8 | 52.2 | 0.4 | 4.0 | 80.0 |
| 6 | <0.1 | 27.3 | 53.3 | 0.4 | 4.0 | 80.6 |
| 7 | <0.1 | 26.7 | 55.5 | 0.5 | 3.7 | 82.2 |
| 8+ | <0.1 | 26.9 | 54.7 | 0.5 | 3.9 | 81.6 |
| 9 | 0.4 | 23.1 | 52.2 | 2.3 | 5.5 | 75.3 |
| 10 | 0.1 | 25.9 | 55.8 | 0.5 | 4.1 | 81.7 |
| 11 | <0.1 | 26.7 | 55.5 | 0.5 | 3.7 | 82.2 |
| 12 | <0.1 | 27.2 | 52.6 | 0.4 | 4.0 | 79.8 |
| 13 | 0.1 | 27.0 | 46.7 | 0.4 | 4.6 | 73.7 |
| 14 | 0.1 | 25.6 | 41.6 | 0.5 | 5.7 | 67.2 |
| 15 | 0.1 | 24.0 | 55.7 | 0.8 | 4.9 | 79.7 |
| 16++ | 0.1 | 22.1 | 52.2 | 1.3 | 8.9 | 74.3 |
| 17++ | 0.2 | 24.5 | 43.7 | 0.9 | 8.6 | 68.2 |
| 18++ | 0.9 | 21.2 | 48.6 | 2.9 | 5.1 | 69.8 |

+isobutene metered in as a liquid
++comparison examples

Table 3

| Time after leaving the reactor hours | Composition of the reaction mixture (% by weight) | | | | |
|---|---|---|---|---|---|
| | aliphatic compounds | mono-butylcresols | di-tertiary-butyl-p-cresol | di-tertiary-butyl-m-cresol | high-boiling compounds |
| 0 | 4.0 | 14.7 | 27.5 | 53.5 | 0.3 |
| 0.5 | 4.5 | 15.7 | 27.5 | 51.8 | 0.5 |
| 1 | 4.7 | 16.8 | 27.5 | 50.6 | 0.4 |
| 2 | 5.2 | 18.7 | 27.5 | 48.3 | 0.3 |
| 4 | 6.5 | 22.4 | 27.4 | 43.4 | 0.3 |

What is claimed is:

1. In a process for the continuous preparation of a di-tert.-butylcresol wherein m- or p-cresol is reacted with isobutene at elevated temperature, using $H_2SO_4$ as catalyst, the improvement which comprises carrying out the process with stepwise addition of isobutene employing 2–5 steps of isobutene addition, the isobutene being introduced in each step into a reaction mixture comprising substantially all of the cresol to be reacted, the total amount of isobutene being introduced stepwise such that less isobutene is introduced in a last step of the process than is introduced in a first step thereof, the process being carried out at a temperature below 80° C. and thereafter deactivating the catalyst, said process further comprising:

A. in the two stepwise addition of isobutene, between 55 and 85% of the total isobutene is introduced in the first step and between 15 and 45% of the total isobutene is introduced in the second step;

B. in the three step isobutene addition, between 35 and 80% of the total isobutene is introduced in the first step, between 4 and 32% of the total isobutene is introduced in the second step, and between 5 and 20% of the total isobutene is introduced in the third step;

C. in the four step isobutene addition, between 30 and 75% of the total isobutene is introduced in the first step, between 10 and 40% of the total isobutene is introduced in the second step, between 5 and 31% of the total isobutene is introduced in the third step, and between 2 and 20% of the total isobutene is introduced in the fourth step; and D. in the five step isobutene addition, between 20 and 70% of the total isobutene is introduced in the first step, between 10 and 40% of the total isobutene is introduced in the second step, between 5 and 30% of the total isobutene is introduced in the third step, between 2 and 20% of the total isobutene is introduced in the fourth step, and between 1 and 15% of the total isobutene is introduced in the fifth step.

2. Process according to claim 1 wherein the reaction is carried out in the temperature range of 50° to 70° C.

3. Process according to claim 1 wherein the reaction is carried out at the same temperature in all the steps.

4. Process according to claim 1 wherein the reaction is carried out in 3 or 4 steps.

5. Process according to claim 1 wherein steps having the same reaction volume are used.

6. Process according to claim 1 wherein the total amount of isobutene employed is so distributed that the amount of isobutene fed into each particular step is less than that fed into the preceding step.

7. Process according to claim 1 wherein the amount of isobutene fed into each particular step is at most half that fed into the preceding step.

8. Process according to claim 1 wherein mono-tert.-butylcresol is used as a partial replacement of cresol and isobutene.

9. Process according to claim 1 wherein less than 3% by weight, based on cresol, of sulfuric acid are used.

* * * * *